US012806158B2

(12) United States Patent
Jackson

(10) Patent No.: US 12,806,158 B2
(45) Date of Patent: Nov. 24, 2026

(54) COMBINATION NASAL AND ORAL THERAPY FOR WEIGHT LOSS

(71) Applicant: Milton S. Jackson, Campbellsville, KY (US)

(72) Inventor: Milton S. Jackson, Campbellsville, KY (US)

( * ) Notice: Subject to any disclaimer, the term of this patent is extended or adjusted under 35 U.S.C. 154(b) by 134 days.

(21) Appl. No.: 18/849,767

(22) PCT Filed: Mar. 13, 2023

(86) PCT No.: PCT/US2023/015078
§ 371 (c)(1),
(2) Date: Sep. 23, 2024

(87) PCT Pub. No.: WO2023/183153
PCT Pub. Date: Sep. 28, 2023

(65) Prior Publication Data

US 2025/0195455 A1 Jun. 19, 2025

Related U.S. Application Data

(60) Provisional application No. 63/323,238, filed on Mar. 24, 2022.

(51) Int. Cl.

| | |
|---|---|
| ***A61K 31/137*** | (2006.01) |
| ***A61K 9/00*** | (2006.01) |
| ***A61K 9/20*** | (2006.01) |
| ***A61K 31/485*** | (2006.01) |
| ***A61K 31/55*** | (2006.01) |
| ***A61K 47/18*** | (2017.01) |
| ***A61P 3/04*** | (2006.01) |

(52) U.S. Cl.
CPC .......... *A61K 31/137* (2013.01); *A61K 9/0043* (2013.01); *A61K 9/0053* (2013.01); *A61K 9/20* (2013.01); *A61K 31/485* (2013.01); *A61K 31/55* (2013.01); *A61K 47/18* (2013.01); *A61P 3/04* (2018.01)

(58) Field of Classification Search
CPC .................................................... A61K 31/137
See application file for complete search history.

(56) References Cited

U.S. PATENT DOCUMENTS

| | | | | |
|---|---|---|---|---|
| 12,611,388 B1 * | 4/2026 | Allen | .................. | A61K 31/137 |
| 2014/0309252 A1 | 10/2014 | Mckinney | | |
| 2019/0216799 A1 | 7/2019 | Weber | | |
| 2020/0179277 A1 | 6/2020 | Jackson | | |
| 2021/0275536 A1 | 9/2021 | Bentz | | |

FOREIGN PATENT DOCUMENTS

| | | |
|---|---|---|
| WO | 2023183153 A1 | 9/2023 |

OTHER PUBLICATIONS

European Patent Office, Extended European Search Report issued in Application No. 23775463.5, 7 pages, dated Feb. 13, 2026.
Gaddie Kishore M et al, "Pharmacotherapy for Patients with Obesity," Clinical Chemistry, vol. 64, No. 1, pp. 118-129, XP093362938, Retrieved from: https://pmc.ncbi.nlm.nih.gov/articles/PMC7379842/pdf/nihms-1610290.pdf; dated Jan. 1, 2018.
International Searching Authority, International Search Report and Written Opinion issued in Application No. PCT/US2023/015078, 22 pages, dated Jul. 19, 2023.

* cited by examiner

*Primary Examiner* — Golam M Shameem
(74) *Attorney, Agent, or Firm* — Gray Ice Higdon

(57) ABSTRACT

A combination therapy including both intranasal and oral solid-form preparations is described. In combination, the intranasal and oral delivery pathways provided an enhancement in appetite suppression and associated weight loss in comparison to either intranasal or oral solid-form therapy alone. It was unexpected that the observed substantial increase and increase in rate of weight loss would be observed for the combination therapy, which on average provided a nearly 12% reduction in total body weight over the three-month trial.

15 Claims, 1 Drawing Sheet

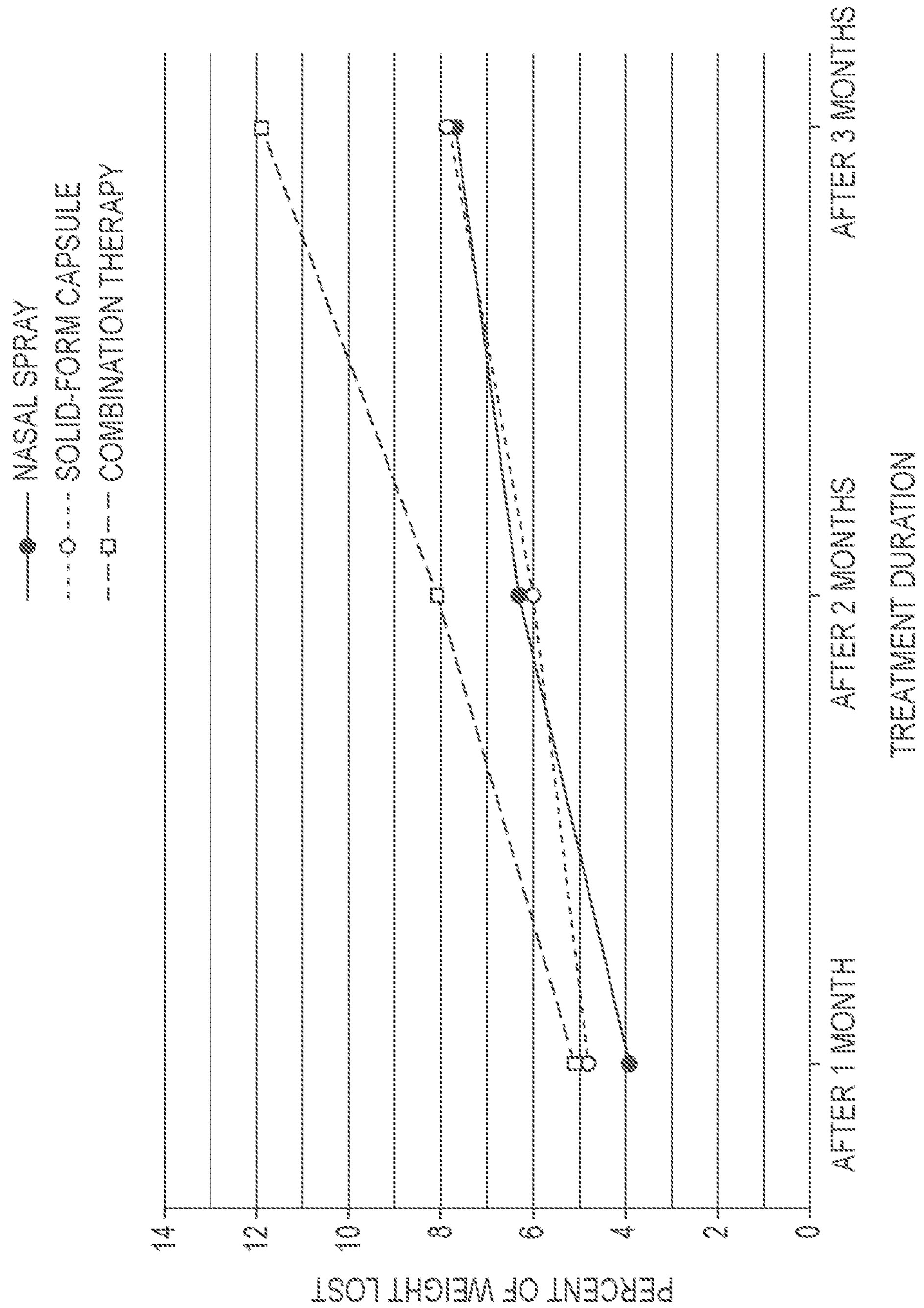
NASAL SPRAY
SOLID-FORM CAPSULE
COMBINATION THERAPY
PERCENT OF WEIGHT LOST
14
12
10
8
6
4
2
0
AFTER 1 MONTH
AFTER 2 MONTHS
AFTER 3 MONTHS
TREATMENT DURATION

COMBINATION NASAL AND ORAL THERAPY FOR WEIGHT LOSS

REFERENCE TO RELATED APPLICATIONS

This application claims the benefit of U.S. Provisional Application No. 63/323,238 entitled "Combination Nasal and Oral Therapy for Weight Loss" filed Mar. 24, 2022, which is incorporated by reference in its entirety.

BACKGROUND

Obesity is one of the greatest health problems in the United States and worldwide, especially from a long-term perspective. There are one hundred million obese or morbidly obese individuals in the United States. There are also one hundred million overweight individuals in the United States. Thus, approximately one-third of the population of the United States is overweight, and another one-third of the population is either obese or morbidly obese. The yearly cost from obesity is estimated to be on the order of $200,000,000,000 to $400,000,000,000. Worldwide, 2,500,000 deaths are attributed to obesity yearly.

Obesity is a consequence of a generally sedentary lifestyle and the fact that individuals "enjoy" an abundance of unhealthy foods. For example, obesity is the second-leading cause of preventable death after tobacco abuse. Obese patients are unable to maintain a healthy lifestyle with necessary increases in activity and exercise along with dietary changes to lose weight.

Weight gain and obesity occur when a person consumes more calories than they burn. The accumulation of fat is a consequence of environmental (eating, activity, behavioral, and social) and genetic factors. Being overweight is defined as having a BMI>30 (BMI=wt. in kg./ht. in m. squared), and morbidly obese is BMI>35. Ideal weight according to the Metropolitan Life Tables (standard source) is BMI<25.

Obesity and related illnesses have tremendous physical, psychological, and financial impact. Present treatments for obesity are expensive, inadequately effective, and have significant risks and side-effects. In addition to the large number of medical problems caused by obesity, being overweight has a negative impact on quality of life.

Obesity continues to be a growing epidemic despite the advances of modern medicine. Dietary and activity changes with both medical and surgical care are not controlling the problem with currently available medical treatments being marginally effective and having significant costs and associated side effects/risks. Surgeries for obesity are generally more effective than medical treatments, but have enormous costs with both short- and long-term risks and complications. Even though obesity is a growing epidemic, medical professionals are spending less time treating and following these patients due to the inadequacy of treatment options and the required time. It is unfortunately ironic that the treatments for the comorbidities of obesity are more effective than treating the underlying weight gain and eating problems.

Mortality rate for a patient with BMI>40 is double that of a normal weight individual. Surgical treatments are indicated for patients failing medical treatment, for BMI>35 with comorbidities, or for BMI>40. It is extremely difficult to quantify or objectify the impact that obesity has on quality of life and lifestyle. Deaths from obesity are due to the comorbid conditions and complications of the excess weight. Obesity causes or contributes to diabetes and insulin resistance, hypertension, heart disease, vascular disease, strokes, dyslipidemia, liver disease, gastroesophageal reflux, urinary incontinence, cellulitis and other infections, obstructive pulmonary disease and respiratory insufficiency, sleep apnea, sexual and other hormone dysfunction, depression, gallbladder disease and dysfunction, and a multitude of orthopedic problems including neck, back, hip, knee, and foot issues and pain. Obesity is a significant contributing factor in cancers of the uterus, breast, ovaries, prostate, colon, esophagus, pancreas, and thyroid, and possibly others. Other medical conditions related to obesity include Cushing's disease, polycystic ovary syndrome, "metabolic syndrome", and psychogenic or genetic eating disorders.

It takes a long time to gain significant weight, and unfortunately it takes significant lifestyle changes over a long time to lose this weight. Even a 10-15% weight loss has health benefits. Long-term and life-long changes and commitments to improve eating and activity are required to lose weight and regain good health and well-being. 3500 kcals are the equivalent of one pound of body weight. For weight loss, the typical diet includes 1200-1800 kcals/day. This should include quality nutrition sources of proteins, vitamins, complex carbohydrates, fiber, and fluids.

Learning to eat the correct amounts of the right foods is imperative to losing weight and regaining health. Burning calories through increased activity and exercise also results in additional burned calories through an increase in base metabolism or Base Metabolic Rate (BMR). Overall weight loss depends on more calories burned than consumed. Burning more calories than are consumed must be maintained for some time to have the success of weight loss and maintenance and regain the health benefits of the lower weight. Looking better, feeling better, and living better and longer are the results.

Existing medical and surgical treatments for obesity are not "fixes" or "answers" to the problem. They are but tools to help achieve the goal of weight loss and regaining health benefits. Present treatments and care fail because they do not extrapolate into the lifelong (eating and activity) habit changes required. Surgery is costly with short- and long-term risks and consequences depending on the procedure and the patient. Eating the proper amounts of the right types of foods is key to addressing the problem of obesity.

The following are examples of existing medical and surgical treatments for obesity:

Medication: BELVIQ
- Generic: Lorcaserin
- Drug Class: Selective Serotonin Agonist
- Schedule IV Approved
- Cost: $200-220/month
- Benefits: Decreases hunger and appetite; increased satiety; 3-5% weight loss/year vs. placebo
- Risks: Significant relapse, withdrawal, medication interaction
- Significant side-effects vs. modest efficacy-rejected by European Medicine Agency
- Side-effects: psychiatric, neurologic, gastrointestinal, cardiologic, endocrine, and hematologic; metabolic issues
- Pregnancy: No
- Children: No Medication: CONTRAVE
- Generic: Buproprion/Naltrexone
- Drug Class: SSRI Antidepressant/Opioid Antagonist Approved
- Cost: $180-210/month
- Benefits: Decreases hunger and cravings; 5% weight loss/year vs. placebo Risks: Medication interaction; withdrawal; metabolic and endocrine abnormalities
Side effects: Neurologic, psychiatric, cardiologic, and gastrointestinal
Pregnancy: No
Children: No Medication: TOPAMAX
Generic: Topiramate
Drug Class: Neurologic
Psychiatric: Not approved
Cost: $10-25/month
Benefits: Decreases hunger and craving
Risks: Minimal, if any efficacy (vs. placebo), and significant side-effects; Interactions including Lithium and alcohol
Side effects: Psychiatric, neurologic, orthopedic, and pulmonary Allergic reactions; migraines; pain syndromes; seizures; metabolic and endocrine abnormalities, glaucoma
Pregnancy: No
Children: No Medication: XENICAL (RX)/ALLI (OTC)
Generic: Orlistat
Drug Class: Lipase inhibitor; Approved
Cost: $180/month
Benefits: Lipase inhibitor decreases fat absorption (most concentrated source of calories) 5% weight loss (vs. placebo)/6 months; net loss approximately 500 kcal/day=1 lb./week
Risks: TIO dosing; severe gastrointestinal distress/dumping; vitamin malabsorption; many medication interactions due to malabsorption problems
Side-effects: Liver, pancreas, gallbladder; complicates and exacerbates gastrointestinal comorbidities
Pregnancy: No
Children: No Medication: QSYMIA
Generic: Phentermine and Topamax
Drug Class: Stimulant/anorectic and seizure Schedule IV; Approved
Cost: $200-220/month
Benefits: Decreases hunger appetite; satiety; 16-33 lb./year weight loss (vs. 6 lb./year placebo)
Risks: Significant side-effects topamax; significant side-effects phentermine; information waiver must be signed due to side-effects; tolerance; withdrawal; hypersensitivity and allergic reactions; medication interactions
Side-effects: psychiatric, neurologic, cardiac and hypertension, gastrointestinal and glaucoma Metabolic and endocrine dysfunction
Pregnant: No
Children: No Medications: ZOLOFT, PROZAC, AND WELLBUTRIN
Generic: Sertraline, Fluoxetine, and Bupropion
Drug Class: SSRI Antidepressants; Not approved
Cost: $10-40/month
Benefits: May treat appetite and hunger; may treat psychogenic eating disorders (ie. Overeating due to depression)
Risks: No evidence of weight loss; no drug trials for weight loss; possible weight gain; has been used inappropriately in substitution for Fenflouramine (PONDIMIN); drug interactions; withdrawal; psychologic and neurologic side-effects
Pregnancy: No
Children: No Medications: ADIPEX, TENUATE, DIDREX, ADIPOST, and BONTRIL
Generic: Phentermine, Diethylpropion, Benzphetamine, and Phendimetrazine
Drug Class: Sympathomimetic; Schedule III and IV Approved for short-term use
Cost: $20-40/month
Benefits: Stimulant; satiety; decreased hunger and appetite; 50% patients have 10% weight loss/12 weeks 80% patients have 5% weight loss/12 weeks; Average 10% weight loss/one year (vs. 3% placebo)
Risks: Addicting; withdrawal; medication interactions; metabolic and endocrine dysfunction
Side-effects: Cardiac, neurologic, psychologic, gastrointestinal, also hematopoietic; Also: insomnia, palpitations, and tremors; most patients rapidly plateau and then regain weight; does not support lifestyle changes (enables dysfunctional lifestyle)
Pregnancy: No
Children: No Medication: GLP-1 Agonists (Glucagon Like Peptide)
Generic: Dulaglutide, Exenatide, Semaglutide, Liraglutide, Albeglutide, and Lixisenatide
Drug Class: Gastrointestinal Peptide Agonist for Diabetes Type 2 and Obesity
Cost: $700-1400/month
Benefits: Average weight loss 2.9 kg./year vs. placebo; increased insulin excretion from pancreas; increased glucose uptake by muscles; decreased glucose production from liver; increased satiety at the hypothalamus; decreased gastric emptying; decreased glucagon excretion from pancreas
Risks: Nausea and vomiting; diarrhea; hypoglycemia; dizziness; headaches; dyspepsia; extreme cost
Contraindications: Allergic and hypersensitivity; some forms of the drub are only available as injectables; medical or surgical gastrointestinal disease Surgical Procedure: SLEEVE GASTRECTOMY
Cost: $10-26K
Description: Removes 80% of stomach
Results: Low post-op/surgical maintenance
Benefits: No foreign body; modest surgery time; decreases hunger; decreases Ghrelin, a "hunger hormone"; approximately 60% weight loss/first year-maintained through 5 years
Risks: Risks of surgery and anesthesia; general gastrointestinal complaints; malnutrition and malabsorption; plateau of weight loss after 6 months-1 year Hospitalization; nonreversible potential sever risks; postoperative diet
Pregnancy: No
Children: No Surgical Procedure: "LAP-BAND SYSTEM"-ADJUSTABLE GASTRIC BANDING
Cost: $9-18K
Description: Laparoscopic or open placement of adjustable restricting gastric band
Results: Forces satiety
Benefits: Approximately 50% weight loss over 2-3 years (3 months-20%) (6 months-30%) (12 months-40%) (2 years-50%)
Risks: Most weight loss plateaus at 2 years; obstructive; greatly restricts diet; foreign body and infection; enabling-does not address abnormal eating behavior Regain weight after removal; slower weight loss than other surgeries; malnutrition; costs of removal or revision; esophago/gastro/intestinal symptoms: pain, nausea, vomiting, reflux and esophagitis, slippage
- Pregnancy: No
- Children: No Surgical Procedure: "ORBERA"-INTRAGASTRIC BALLOON
- Cost: $6-8K
- Description: Endoscopic placement of intragastric balloon under anesthesia
- Benefits: 20 lb. weight loss/6 months; noninvasive; 300% more effective than diet and exercise; easily reversible; years of experience-220,000 placed worldwide
- Risks: Procedural/placement Obstruction symptoms; no long-term benefit-regain weight; multiple nonspecific gastrointestinal complaints; does not directly address abnormal eating behaviors; contraindicated with most gastrointestinal conditions
- Pregnancy: No
- Children: No Surgical Procedure: "ASPIRE ASSIST"-GASTROSTOMY WITH GASTRIC DRAINAGE
- Cost: $8-13K
- Description: Surgical gastrostomy with application of drainage/evacuation device
- Results: Drains 30% postprandial gastric contents
- Same procedure as Gastrostomy Placement-many years of experience Newest approved procedure
- Reversible
- 300% more effective than diet and exercise
- Risks: Minor surgery
- Abdominal tube/hole with hardware/mechanism
- Does not address abnormal eating behavior (enables-essentially is medical bulimia)
- Nonspecific gastrointestinal complaints
- Open wound/hole in abdomen No benefit after discontinued
- Pregnancy: No
- Children: No Surgical Procedure: "VBLOC"-VAGAL NERVE BLOCKADE
- Cost: $20-30K
- Description: Implanted pulse generator in chest, lead wires to vagus nerve, and controller/charger/transmitter-Enteromedics
- Results: 9% weight loss/12 months; satiety; less hunger; reversible; modestly invasive
- Risks: Surgical and anesthesia; marginally more effective than medical (diet and exercise); foreign body; nonspecific gastrointestinal complaints; does not address abnormal eating behavior; regain weight after discontinued; bloating symptoms with slowed digestion; New-unknown long-term risks or side effects
- Pregnancy: No
- Children: No Surgical Procedure: ROUX-EN-Y GASTRIC BYPASS
- Cost: $15-55K
- Description: Open or Laparoscopic anastomoses gastric pouch to jejunum and the gastric remnant/duodenum to the distal jejunum
- Results: "Gold Standard" of bariatric surgery; 60-80% excess weight loss/18 months 50-55% excess weight loss/10 years; satiety; many years of experience performing procedure and then treating/following postoperatively
- Risks: Surgery and Anesthesia with relatively long procedure; hospitalization; malabsorption and malnutrition; postoperative surgical risks with extensive procedure; nonspecific gastrointestinal complaints; diet restriction; permanent; eventual weight gain as tolerance develops and eating disorders return
- Pregnancy: No
- Children: No Surgical Procedure: BILIOPANCREATIC DIVERSION WITH DUODENAL SWITCH
- Cost: $24-32K
- Description: Open or laparoscopic partial gastrectomy, cholecystectomy, partial duodenectomy, anastomosis of stomach to ileum and duodenum to distal ileum.
- Results: Most weight loss of any procedure: 30% excess weight loss/3 months; 45% excess weight loss/6 months; 65% excess weight loss/12 months 70% weight loss long term; satiety; less ulcer and dumping risks as compared to gastric bypass
- Risks: Major/extensive surgery and anesthesia; short and long term surgical complications; malabsorption and malnutrition; nonspecific gastrointestinal symptoms; highest complication rate; permanent hospitalization; prolonged recovery: 4-8 weeks
- Pregnancy: No
- Children: No There is accordingly a long-felt need for a safe and effective drug therapy that suppresses appetite to treat obesity. While drug based appetite suppressant therapies exist, a combined therapy providing enhanced weight loss in relation to conventional drug therapies would be advantageous. The combined therapies of the invention overcome at least one of the disadvantages associated with conventional drug therapy obesity treatments.

SUMMARY

In one aspect, the invention provides a method of inducing weight loss and treating obesity in a human subject, the method including administering orally an oral solid-form preparation including a therapeutically effective amount of phentermine and naltrexone; and administering intranasally an intranasal preparation including a therapeutically effective amount of a histamine antagonist, a local anesthetic, and excipients providing enhanced persistence and stability of the intranasal preparation in the nasal cavity, where the subject experiences appetite suppression, and where the subject experiences a reduction in total body weight in response to the appetite suppression during the treatment.

In another aspect of the invention, there is a method of treating obesity in a human subject, the method including administering orally an oral solid-form preparation comprising a therapeutically effective amount of phentermine and naltrexone; and administering intranasally an intranasal preparation comprising a therapeutically effective amount of a histamine antagonist, a local anesthetic, and excipients providing enhanced persistence and stability of the intranasal preparation in the nasal cavity, where the subject experiences a reduction in total body weight during the treatment.

In another aspect of the invention, there is a method for inducing weight loss in a subject in need of weight loss, the method including administering orally an oral solid-form preparation comprising a therapeutically effective amount of phentermine and naltrexone; and administering intranasally an intranasal preparation comprising a therapeutically effective amount of a histamine antagonist, a local anesthetic, and excipients providing enhanced persistence and stability of the intranasal preparation in the nasal cavity, where the subject experiences weight loss.

In another aspect of the invention, there is a method for inducing anosmia in a human subject, the method including administering orally an oral solid-form preparation comprising a therapeutically effective amount of phentermine and naltrexone; and administering intranasally an intranasal preparation comprising a therapeutically effective amount of a histamine antagonist, a local anesthetic, and excipients providing enhanced persistence and stability of the intranasal preparation in the nasal cavity, where the subject experiences anosmia.

In another aspect of the invention, there is a method for suppressing appetite in a human subject, the method including administering orally an oral solid-form preparation comprising a therapeutically effective amount of phentermine and naltrexone; and administering intranasally an intranasal preparation comprising a therapeutically effective amount of a histamine antagonist, a local anesthetic, and excipients providing enhanced persistence and stability of the intranasal preparation in the nasal cavity, where the subject experiences appetite suppression.

Other methods, features, and advantages of the invention will be, or will become, apparent to one with skill in the art upon examination of the following figures and detailed description. It is intended that all such additional methods, features, and advantages be included within this description, be within the scope of the invention, and be protected by the claims that follow. The scope of the present invention is defined solely by the appended claims and is not affected by the statements within this summary.

BRIEF DESCRIPTION OF THE FIGURES

The invention can be better understood with reference to the following drawings and description.

FIG. 1 graphically represents the treatment results provided in Table II summarizing the weight loss results of treatment groups of patients using the oral solid-form preparation, the nasal preparation, and combination therapy.

DETAILED DESCRIPTION

A combination therapy including both intranasal and oral solid-form preparations is described. In combination, the intranasal and oral delivery pathways provided an enhancement in appetite suppression and associated weight loss in comparison to either intranasal or oral solid-form therapy alone. It was unexpected that the observed substantial increase and increase in rate of weight loss would be observed for the combination therapy, which on average provided a nearly 12% reduction in total body weight over the three-month trial.

Intranasal Preparation

The intranasal preparation includes a histamine antagonist, a local anesthetic, and at least one pharmaceutically acceptable excipient suitable for intranasal delivery that enhances persistence and stability of the preparation in the nasal cavity. The intranasal preparation is in a free-flowing liquid state at ambient temperature up to approximately 30 degrees Celsius, but exists predominantly in gel form (as a semirigid colloidal dispersion) at the temperature of a superior portion of the nasal cavity of a human subject, thus is predominantly in gel form from approximately 34 degrees Celsius up to the temperature of the superior portion of the nasal cavity of a human subject.

The intranasal preparation is configured to remain in the superior portion of the nasal cavity for a period of at least five minutes following the intra nasal spraying of the preparation. Preferably, less than 25% by weight of the intranasal preparation volume sprayed into the nostril exits the nostril through the external aperture of the nostril during a five-minute interval immediately following the spraying of the intranasal preparation into the nostril.

The histamine antagonist preferably is chosen from azelastine, a pharmaceutically acceptable salt of azelastine, olopatadine, a pharmaceutically acceptable salt of olopatadine, and combinations thereof. More preferably, the pharmaceutically acceptable salt of azelastine is azelastine hydrochloride (AZ) and the pharmaceutically acceptable salt of olopatadine is olopatadine hydrochloride (OL). A therapeutically effective dose of the histamine antagonist is believed to be from 0.1 mg to 0.2 mg per dose, preferably with three doses given per day before meals.

The local anesthetic preferably is chosen from lidocaine, pharmaceutically acceptable salts of lidocaine, and combinations thereof. More preferably, the pharmaceutically acceptable salt of lidocaine is lidocaine hydrochloride (LD). A therapeutically effective dose of the local anesthetic is believed to be from 0.5 mg to 2.5 mg per dose, preferably with three doses given per day before meals.

The intranasal suitable excipients providing the desired liquid to predominantly gel phase transition include those chosen from pectin, methylcelluloses, blends of microcrystalline cellulose/sodium carboxymethylcellulose, glycerol esters of hydrogenated rosin, and combinations thereof. Flavorings also may be added to provide the product with a more desirable smell/taste. Additional excipients may be used.

Preferably, the pectin is a low methyl ester pectin, such as LM-104 AS-Z or LM-12 CG-Z as available from CP Kelco, Lille Skensved, Denmark. Sodium citrate and/or citric acid solutions may be used to control the pH of the hydrated pectin from 4.0 to 4.5. Preferable methylcelluloses are METHOCEL™ A 15 LV, as available from Sigma-Aldrich and DOW or Methylcellulose A4M as available from Dow, with Methylcellulose A4M being more preferred. A preferable microcrystalline cellulose/sodium carboxymethylcellulose is AVICEL™ RC-591 as available from FMC Corporation or IFF/DuPont.

The intranasal preparation preferably includes approximately 54% USP purified water (w/w). The intranasal preparation may include Purified Water, USP, at a concentration from 20% to 80% w/w, or from 30% to 70% w/w, or from 40% to 60% w/w, or from 45% to 55% w/w.

The intranasal preparation preferably includes approximately 0.74% pectin (w/w). The intranasal preparation may include pectin at a concentration from 0.1% to 1.5% w/w, or from 0.2% to 1.25% w/w, or from 0.3% to 1.1% w/w, or from 0.4% to 1% w/w, or from 0.5% to 0.9% w/w, or from 0.6% to 0.8% w/w.

The intranasal preparation preferably includes approximately 1.58% METHOCEL™ A15 Premium LV (w/w). The intranasal preparation may include METHOCEL™ A15 Premium LV at a concentration from 0.25% to 4% w/w, or from 0.5% to 3% w/w, or from 0.75% to 2.25% w/w, or from 1% to 2% w/w, or from 1.25% to 1.75% w/w, or from 1.4% to 1.6% w/w.

The intranasal preparation preferably includes approximately 0.44% METHOCEL™ A4M Premium LV (w/w). The intranasal preparation may include METHOCEL™ A4M Premium LV at a concentration from 0.05% to 1% w/w, or from 0.1% to 0.9% w/w, or from 0.2% to 0.8% w/w, or from 0.3% to 0.7% w/w, or from 0.4% to 0.6% w/w.

The intranasal preparation preferably includes approximately 24.60% 0.1 M sodium citrate aqueous solution, pH 6.0. The intranasal preparation may include 0.1 M sodium citrate aqueous solution, pH 6.0, at a concentration from 10% to 40% w/w, or from 15% to 35% w/w, or from 20% to 30% w/w, or from 22.5% to 27.5% w/w, or from 24% to 25% w/w.

The intranasal preparation preferably includes approximately 9.00% of a 70% (w/w) sorbitol aqueous solution (w/w). The intranasal preparation may include a 70% (w/w) sorbitol aqueous solution at a concentration from 1% to 20% w/w, or from 2% to 17% w/w, or from 4% to 15% w/w, or from 6% to 12% w/w, or from 8% to 10% w/w.

The intranasal preparation preferably includes approximately 3.28% polyethylene glycol 400 (PEG 400) (w/w). The intranasal preparation may include polyethylene glycol 400 (PEG 400) at a concentration from 0.5% to 10% w/w, or from 0.75% to 8% w/w, or from 1% to 6% w/w, or from 2% to 5% w/w, or from 3% to 4% w/w.

The intranasal preparation preferably includes approximately 0.12% E10M hydroxypropyl methylcellulose (w/w). The intranasal preparation may include E10M hydroxypropyl methylcellulose at a concentration from 0.02% to 0.2% w/w, or from 0.04% to 0.18% w/w, or from 0.05% to 0.16% w/w, or from 0.08% to 0.14% w/w, or from 0.1% to 0.13% w/w.

The intranasal preparation preferably includes approximately 0.40% sodium chloride (w/w). The intranasal preparation may include sodium chloride at a concentration from 0.05% to 2% w/w, or about 0.1% to 1.5% w/w, or from 0.2% to about 1% w/w, or from 0.3% to 0.6% w/w, or from 0.35% to 0.45% w/w.

The intranasal preparation preferably includes approximately 4.08% mannitol (w/w). The intranasal preparation may include mannitol at a concentration from 0.5% to 20% w/w, or from 1% to 15% w/w, or from 2% to 10% w/w, or from 3% to 7.5% w/w, or from 3.5% to 4.5% w/w.

The intranasal preparation preferably includes approximately 0.01% butylated hydroxytoluene (w/w). The intranasal preparation may include butylated hydroxytoluene at a concentration from 0% to 0.02% w/w, or from 0.0025% to 0.0175% w/w, or from 0.005% to 0.015% w/w, or from 0.0075% to 0.0125% w/w.

The intranasal preparation preferably includes approximately 0.12% of a glycerol ester of a hydrogenated rosin (w/w). The intranasal preparation may include a glycerol ester of a hydrogenated rosin at a concentration from 0.02% to 0.22% w/w, or from 0.05% to 0.19% w/w, or from 0.08% to 0.16% w/w, or from 0.1% to 0.14% w/w.

The intranasal preparation preferably includes approximately 0.12% of oleic acid (w/w). The intranasal preparation may include oleic acid at a concentration from 0.05% to 0.19% w/w, or from 0.08% to 0.16% w/w, or from 0.1% to 0.14% w/w.

The intranasal preparation preferably includes approximately 1.00% of lidocaine hydrochloride (w/w). The intranasal preparation may include lidocaine hydrochloride at a concentration from 0.25% to 1.75% w/w, or from 0.5% to 1.5% w/w, or from 0.75% to 1.25% w/w.

The intranasal preparation preferably includes approximately 0.15% of azelastine hydrochloride (w/w). The intranasal preparation may include azelastine hydrochloride at a concentration from 0.05% to 0.25% w/w, or from 0.1% to 0.2% w/w.

The intranasal preparation preferably includes approximately 0.33% flavorants (w/w). The intranasal preparation may include flavorants at a concentration from 0.0% to 0.6% w/w, or from 0.16% to 0.5% w/w. Preferable flavorants include lavender and lemon, but other flavorants compatible with the other preparation constituents and temperature-based phase change may be used.

An exemplary formulation of the intranasal preparation is provided below in Table I.

TABLE I

| Preparation Component | Amount in grams per 500 grams of Preparation | Measurement Unit | % of Preparation (w/w) |
|---|---|---|---|
| Purified Water, USP | 269.6 | grams | 53.924 |
| Pectin (CP Kelco) | 3.690 | grams | 0.738 |
| Methocel ® A15 Premium LV (DOW) | 7.890 | grams | 1.578 |
| Methocel ® A4M Premium LV (DOW) | 2.220 | grams | 0.444 |
| pH 6.0 0.1M Sodium Citrate Solution | 123.0 | mL | 24.600 |
| Sorbitol Solution (70%) (Spectrum) | 45.000 | grams | 9.000 |
| Polyethylene Glycol 400 (Spectrum) | 16.400 | grams | 3.280 |
| E10M Hydroxypropyl Methylcellulose (DOW) | 0.593 | grams | 0.119 |
| Sodium Chloride (JT Baker) | 2.020 | grams | 0.404 |
| Mannitol | 20.400 | grams | 4.080 |
| Benzalkonium Chloride (Science Lab) | 0.500 | grams | 0.100 |
| Butylated Hydroxytoluene (Spectrum) | 0.050 | grams | 0.010 |
| Glycerol Ester of Hydrogenated Rosin (Newport) | 0.603 | grams | 0.121 |
| Oleic Acid (TCI) | 0.603 | grams | 0.121 |
| Lidocaine HCl | 5.000 | grams | 1.000 |
| Azelastine HCl | 0.750 | grams | 0.150 |
| Lavender Flavor WONF, Natural, Rebertet | 0.840 | grams | 0.168 |
| Lemon Flavor WONF, Natural, Rebertet | 0.820 | grams | 0.164 |
| Formulation Total | 500.0 | grams | 100.0 |

In use, the intranasal preparation is preferably sprayed sequentially into both nasal cavities of a human subject. The preparation gels in situ in the superior portion of the nasal cavity and forms a "gel plug", effectively blocking passage of odorant molecules. In addition to the blocking function of the gel, the local anesthetic in the preparation causes sufficient blocking of olfactory nerve impulses within the nasal cavity so the subject's sensation of food-derived odorants is diminished, leading to a decreased desire to consume food. The histamine antagonist component of the preparation dries the nasal mucosa of the nasal cavity to delay removal of the gel plug and is believed to further assist the local anesthetic in blocking the olfactory nerve impulses. Thus, the preparation reduces the subject's sensation of food-derived odorants both pharmacologically at the nerve level with an anesthetic and by physically blocking the odor receptors with the gel plug, while simultaneously using the histamine antagonist to prevent mucosal flushing of the anesthetic or gel plug from the odor receptors.

Oral Solid-Form Preparation

The oral solid-form preparation includes naltrexone, phentermine, and excipients suitable for a pharmaceutical oral solid-form preparation. The tablet or capsule includes 1.5 mg, 3.0 mg, or 4.5 mg of naltrexone to provide a therapeutically effective amount of naltrexone hydrochloride from 1.5 mg to 4.5 mg per day. The naltrexone may be provided by naltrexone base having the molecular formula $C_{20}H_{23}NO_4$ and CAS number 16590-41-3 or by a naltrexone salt, such as naltrexone hydrochloride having the having molecular formula $C_{20}H_{23}NO_4{\cdot}HCl$ and CAS number 16676-29-2, as dictated by context and by usage in the pharmaceutical and medical arts. Preferably, naltrexone hydrochloride is used.

The oral solid-form preparation includes 15 mg, 30 mg, or 37.5 mg of phentermine to provide a therapeutically effective amount of phentermine from 15 mg to 37.5 mg per day. The phentermine may be provided by phentermine base, having molecular formula $C_{10}H_{15}N$ and CAS number 122-09-8, or by a phentermine salt, such as phentermine hydrochloride, having molecular formula $C_{10}H_{15}N{\cdot}HCl$ and CAS number 1197-21-3, as dictated by context and by usage in the pharmaceutical and medical arts. Preferably, phentermine hydrochloride is used.

Thus, the oral solid-form is preferably formulated for once-per-day, or twice-per-day dosing based on the therapeutically effective amounts of naltrexone and phentermine desired.

An exemplary oral solid-form including a therapeutically effective amount of naltrexone and phentermine with excipients was formed to produce 100 size #1 capsules by combining Avicel PH105 (microcrystalline cellulose), sourced from Letco Medical, 23.976 g; phentermine hydrochloride USP, sourced from Medisca, 1.5 g; naltrexone hydrochloride USP, sourced from Letco Medical, 0.15 g; blue food coloring, sourced from Letco Medical, 0.024 g; and size #1 capsules, sourced from Letco Medical. Thus, each capsule included the minimum therapeutically effective dose of the naltrexone and phentermine. A tablet as opposed to capsule oral solid-form could similarly be made as known in the pharmaceutical arts.

Combination Therapy

The intranasal preparation was used in combination with the oral solid-form preparation, thus as a combination therapy, to provide enhanced weight loss in relation to the nasal preparation or the oral solid-form preparation alone.

For the oral solid-form preparation a first group of patients were asked to orally consume a capsule including 15 mg of phentermine and 1.5 mg of naltrexone once daily for seven to ten days (tolerance period), and then twice daily for the remainder of the treatment period. The patients were asked to self-administer the capsules one to two hours before lunch and/or dinner depending on the tolerance or treatment period. A second group of patients were asked to orally consume a single capsule including 37.5 mg of phentermine and 3 mg of naltrexone once daily.

Weight loss was experienced by both groups of a three-month trial with the oral solid-form preparation. As a percentage of pre-trial weight, on average, both solid-form groups of patients experienced a 4.8% (w/w) total weight loss after one month, a 6.0% (w/w) total weight loss after two months, and a 7.9% (w/w) total weight loss after three months. A statistically significant difference in weight loss was not observed between the first and second group of patients. Thus, the therapeutically effective amount of naltrexone hydrochloride and phentermine hydrochloride was determined to be deliverable split between two daily doses or as a single daily dose.

For the nasal preparation, a third group of patients were asked to administer one spray into each nostril before meals. Each spray included approximately 100 microliters (~0.1 gram) of the nasal preparation, with each spray including approximately 1 mg of lidocaine hydrochloride as the local anesthetic and approximately 0.15 mg of azelastine hydrochloride as the histamine antagonist. This group of patients were not able to take the oral solid-form preparation due to choice, not meeting the criteria to take phentermine, or contraindications to take phentermine or naltrexone.

Weight loss was experienced by this nasal only third group during the three-month treatment period. As a percentage of pre-trial weight, on average, this group of patients experienced a 3.9% (w/w) total weight loss after one month, a 6.3% (w/w) total weight loss after two months, and a 7.7% (w/w) total weight loss after three months.

For a fourth combination therapy group of patients the intranasal preparation was requested to be added to the single capsule dosing regimen of the second patient group, where patients were asked to introduce one spray of the nasal preparation into each nostril before meals.

Weight loss was experienced by this combination therapy fourth group during the three-month treatment period. As a percentage of pre-trial weight, on average, this group of patients experienced a 5.1% (w/w) total weight loss after one month, a 8.1% (w/w) total weight loss after two months, and an 11.9% (w/w) total weight loss after three months. Thus, the combination therapy can provide an at least 4% reduction in total body weight after two months of treatment and a greater than 8% reduction in total body weight after three months of treatment, with a greater than 10% reduction in total body weight expected after three months of treatment.

Table II below summarizes the weight loss results of these four treatment groups of patients using the oral solid-form preparation, the nasal preparation, and combination therapy. Of note is that all patients in the four treatment groups had failed other diet and exercise programs, most had failed other medicine treatment programs, and five were surgical recidivists that subsequently gained weight after weight loss surgery. All patients were followed monthly in a clinic and met Federal/State Standard-of-Care Prescribing Guidelines regarding indications and compliance.

TABLE II

| Treatment | After 1 Month | After 2 Months | After 3 Months |
|---|---|---|---|
| Oral Solid-Form | 4.8% | 6.0% | 7.9% |
| Nasal Preparation | 3.9% | 6.3% | 7.7% |
| Combination | 5.1% | 8.1% | 11.9% |

FIG. 1 graphically represents the treatment results provided in Table II summarizing the weight loss results of the treatment groups of patients using the oral solid-form preparation, the nasal preparation, and the combination therapy. The combination therapy of the oral solid-form preparation in combination with the nasal preparation resulted in significantly superior weight loss over the three-month trial.

Unexpectedly, the addition of the intranasal preparation to the oral solid-form preparation caused an acceleration in the rate of weight loss at approximately two months that continued to increase through the three-month trial end in relation to the oral solid-form or nasal preparations alone. While both the oral solid-form and intranasal preparations increased weight loss over the three-month trial, the increase was at a relatively constant rate, with a slight decrease in rate for the nasal preparation during the two- to three-month period.

At the end of the three-month treatment period the average total weight loss for the oral solid-form alone was 7.9% (w/w) and the average total weight loss for the nasal preparation alone was 7.7% (w/w), while that of the combination therapy was nearly 12%. The nearly 12% weight loss observed for the combination therapy was an approximate 60% increase in weight loss in relation to either the oral solid-form or nasal preparations alone over the three-month treatment period.

The enhancement in weight loss provided by the combination therapy between two and three months was unexpected considering the one- and two-month data where the oral solid-form provided a 4.8% (w/w) or 6.0% (w/w) total weight loss and the nasal preparation provided a 3.9% (w/w) or 6.3% (w/w) total weight loss in relation to the approximately 6% (w/w) or 8.1% (w/w) total weight loss provided by the combination therapy. Thus, at the one- and two-month periods the combination therapy provided a relatively small 30% increase in weight loss in relation to the approximately 60% increase in weight loss observed at three-months.

In addition to this unexpected acceleration in the rate of weight loss after two-months, it also was unknown whether the combination therapy would provide any benefit in relation to the oral solid-form and nasal preparations alone. Due to the unpredictable nature of drug interaction and effect on the human body, it could have also been the case that the combination therapy did nothing more from a weight loss perspective than either of the oral solid-form or nasal preparations in isolation. The combination therapy also could have resulted in decreased weight loss in relation to the oral or nasal preparations alone as a slight decrease in the rate of weight loss was observed for the nose spray during the two- to three-month test period. Instead, the desired 10% total weight loss for a human subject over a year was more than achieved in three-months with the combination therapy with a weight loss rate that was continuing to accelerate at the three-month trial end.

To provide a clear and more consistent understanding of the specification and claims of this application, the following definitions are provided.

Unless otherwise indicated, all numbers expressing quantities of ingredients, properties such as amounts, and the like used in the specification and claims are to be understood as indicating both the exact values as shown and as being modified by the term "about". Thus, unless indicated to the contrary, the numerical values of the specification and claims are approximations that may vary depending on the desired properties sought to be obtained and the margin of error in determining the values. At the very least, and not as an attempt to limit the application of the doctrine of equivalents to the scope of the claims, each numerical parameter should at least be construed considering the margin of error, the number of reported significant digits, and by applying ordinary rounding techniques.

Unless the context clearly dictates otherwise, where a range of values is provided, each intervening value to the tenth of the unit of the lower limit between the lower limit and the upper limit of the range is included in the range of values.

The term "therapeutically effective amount" refers to the amount of a compound that is sufficient to elicit the biological or medical response of a cell, tissue, system, animal, or human that is being sought by a researcher, veterinarian, medical doctor, or clinician.

Administered "in combination" or "co-administration," refers to administration of the oral solid-form preparation and the intranasal preparation concomitantly in different compositions or sequentially in either order. For sequential administration to be considered administration "in combination" or "co-administration," the oral solid-form preparation and the nasal spray preparation are administered separated by a time interval that permits the resultant beneficial effect for weight loss.

The term "subject" refers to a mammalian animal. The terms "subject" and "patient" are used interchangeably in reference, for example, to a mammalian subject, such as a human patient.

The terms "treat," "treating," and "treatment" are meant to include alleviating or abrogating obesity or one or more of the symptoms associated with obesity; or suppressing appetite to alleviate or eradicate the cause(s) of obesity.

The terms "a", "an", and "the" used in the specification claims are to be construed to cover both the singular and the plural, unless otherwise indicated or contradicted by context. No language in the specification should be construed as indicating any non-claimed element to be essential to the practice of the invention.

While various aspects of the invention are described, it will be apparent to those of ordinary skill in the art that other embodiments and implementations are possible within the scope of the invention. Accordingly, the invention is not to be restricted except considering the attached claims and their equivalents.

The invention claimed is:

1. A method of inducing weight loss and treating obesity in a human subject, the method comprising: administering orally an oral solid-form preparation including a therapeutically effective amount of phentermine and naltrexone; and administering intranasally an intranasal preparation including a therapeutically effective amount of a histamine antagonist, a local anesthetic, and excipients providing enhanced persistence and stability of the intranasal preparation in the nasal cavity, where the subject experiences appetite suppression, and where the subject experiences a reduction in total body weight in response to the appetite suppression during a treatment.

2. The method of claim 1, where the histamine antagonist is chosen from azelastine, a pharmaceutically acceptable salt of azelastine, olopatadine, a pharmaceutically acceptable salt of olopatadine, and combinations thereof.

3. The method of claim 1, where the therapeutically effective amount of the histamine antagonist is from 0.1 mg to 0.2 mg per dose and the therapeutically effective amount of the local anesthetic is from 0.5 mg to 2.5 mg per dose.

4. The method of claim 1, where the local anesthetic is chosen from lidocaine, pharmaceutically acceptable salts of lidocaine, and combinations thereof.

5. The method of claim 1, where the therapeutically effective amount of the naltrexone is from 1.5 mg to 4.5 mg per day and the therapeutically effective amount of the phentermine is from 15 mg to 37.5 mg per day.

6. The method of claim 1, where the administering of the oral solid-form preparation is once-per-day or twice-per-day and the administering of the intranasal preparation is before meals.

7. The method of claim 1, where the subject experiences an at least 4% reduction in total body weight after two months of treatment, or a greater than 8% reduction in total body weight after three months of treatment, or preferably a greater than 10% reduction in total body weight after three months of treatment.

8. The method of claim 1, where the method further includes inducing anosmia in the subject resulting in a decreased desire to consume food.

9. The method of claim 1, where the excipients providing enhanced persistence and stability of the intranasal preparation in the nasal cavity are configured to remain in the superior portion of the nasal cavity for a period of at least five minutes following the administering intranasally.

10. The method of claim 1, where less than 25% by weight of an intranasal preparation volume administered intranasally exits a nostril through an external aperture of the nostril during a five-minute interval immediately following the administering intranasally.

11. The method of claim 1, where the intranasal preparation is administered sequentially through spraying into both nasal cavities of the human subject.

12. The method of claim 1, where the excipients undergo a liquid to gel phase transition when contacting a superior portion of the nasal cavity to form a gel plug within the nasal cavity.

13. The method of claim 12, where the gel plug effectively blocks passage of odorant molecules within the nasal cavity and the local anesthetic causes blocking of olfactory nerve impulses within the nasal cavity.

14. The method of claim 12, where the histamine antagonist dries nasal mucosa of the nasal cavity to delay removal of the gel plug from the nasal cavity.

15. The method of claim 12, where the excipients are chosen from pectin, methylcelluloses, blends of micro crystalline cellulose/sodium carboxymethylcellulose, glycerol esters of hydrogenated rosin, and combinations thereof.

* * * * *